United States Patent [19]
Vit

[11] B 3,991,107
[45] Nov. 9, 1976

[54] HALOAMINE TRANSFER

[75] Inventor: Jaroslav Vit, Belle Mead, N.J.

[73] Assignee: National Patent Development Corporation, New York, N.Y.

[22] Filed: Oct. 26, 1972

[21] Appl. No.: 301,143

[44] Published under the second Trial Voluntary Protest Program on January 27, 1976 as document No. B 301,143.

[52] U.S. Cl. ..................... 260/534 R; 260/112.5 R; 260/309; 260/326.14 T; 260/326.2; 260/404; 260/508; 260/513 N; 260/513.6; 260/518 A; 260/519; 260/534 C; 260/534 E; 260/534 G; 260/534 L; 260/534 M; 260/534 S; 260/584 R; 424/53; 424/54

[51] Int. Cl.² ......................................... C07C 85/04

[58] Field of Search ........ 260/534 R, 534 G, 534 L, 260/534 C, 534 M, 534 S, 534 E, 518 A, 404, 583 NH, 519, 326.2, 326.14 T, 309, 112.5

[56] References Cited
UNITED STATES PATENTS 3,137,728   6/1964   Reid ............................... 260/534 R

*Primary Examiner*—Vivian Garner
*Attorney, Agent, or Firm*—Cushman, Darby & Cushman

[57] ABSTRACT

N-haloamines also containing a hydroxy group, a sulfonic acid group, an N-acyl group or a carboxylic acid group are prepared by reacting an amine with a different N-haloamine to form the N-haloamine of the free amine.

12 Claims, No Drawings

HALOAMINE TRANSFER

The present invention relates to the formation of N-monohaloamines.

N-monohaloamines also containing a hydroxy group, a sulfonic acid group, an N-acetyl group or a carboxylic acid group are useful for many purposes. Thus they are useful in treating teeth to remove caries and plaque, prevent the formation of calculus and to brighten teeth.

Many of these N-monohaloamines which are most useful for such purposes are relatively unstable and must be prepared in situ. It has now been found that N-haloamine compounds of the type specified can be readily prepared by simply mixing in aqueous solution the corresponding amine with a more stable N-haloamine of the type specified.

On the other hand if the two N-haloamines are of substantially the same stability the resulting product is a mixture of the starting N-haloamine, and the haloamine formed. Of course there is also present any unreacted amine as well as the amine remaining from the compound which has lost its halogen. The halogen atoms have an atomic weight of 35 to 127, i.e. They are chlorine, bromine and iodine. There is no harm in having such amine present and in fact for the uses mentioned while there can be used the N-haloamine by itself preferably there is present free amine e.g., in an amount up to 15 moles per mole haloamine and preferably in an amount of 6 to 8 moles per mole of haloamine.

The second N-monohaloamine has a stability in aqueous solution of at least almost the stability of the first N-monohaloamine.

As the nitrogen compounds compounds there can be used either inorganic compounds such as sulfamic acid or organic compounds containing 2 to 11 carbon atoms, e.g. glycine, sarcosine, alpha-aminoisobutyric acid, taurine, 2-aminoethanol, N-acetylglycine, alanine, beta-alanine, serine, phenyl alanine, norvaline, leucine, isoleucine, proline, hydroxyproline, omega amino-undecanoic acid, aspartic acid, glutamic acid, glutamine, asparagine, valine, tyrosine, threonine, cysteine, cystine, methionine, glutamine, tryptophane, histidine, arginine, lysine, alpha-aminobutyric acid, gamma-amino-butyric acid, alpha, epsilon diamino pimelic acid, ornithine, hydroxylysine, anthranilic acid, p-aminobenzoic acid, sulfanilic acid, orthanilic acid, phenyl sulfamic acid, aminopropanesulfonic acid, 2-aminoethanol, 2-aminopropanol, diethanolamine, ethylenediamine tetraacetic acid (EDTA) nitrilotriacetic acid, and aminomethanesulfonic acid.

Examples of N-halo compound include N-chloroglycine, N-bromoglycine, N-iodoglycine, N-chlorosarcosine, N-bromosarcosine, N-iodosarcosine, N-chloro alpha amino isobutyric acid, N-chlorotaurine, N-bromotaurine, N-iodotaurine, N-chloro aminomethanesulfonic acid, N-chloro-N-acetyl glycine, N-chloroethanolamine, N-bromo-N-acetyl glycine, N-chloroalanine, N-chloro beta alanine, N-bromo beta alanine, N-chloroserine, N-bromoserine, N-iodoserine, N-chloro-N-phenylalanine, N-chloroisoleucine, N-chloro-norvaline, N-chloroleucine, N-bromoleucine, N-iodoleucine, N-chloroproline, N-bromoproline, N-iodoproline, N-chloro hydroxyproline, N-chloro omega aminoundecanoic acid, N-chloroaspartic acid, N-bromoaspartic acid, N-chloroglutamic acid, N-iodoglutamic acid, N-chlorovaline, N-chlorotyrosine, N-bromo-tyrosine, N-iodotyrosine, N-chlorothreonine, N-chlorocysteine, N-chlorocystine, N-chloromethionine, N-chlorohistidine, N-chloroarginine, N-chloroglutamine, N-bromoglutamine, N-chlorolysine, N-chloro gamma aminobutyric acid, N-chloro alpha, epsilon diaminopimelic acid, N-chloro-ornithine, N-chloro hydroxylysine, N-chloroanthranilic acid, N-chloro p-aminobenzoic acid, N-chlorosulfanilic acid, N-chloro phenylsulfamic acid, N-chloro aminopropanesulfonic acid, N-chloro-propanolamine, N-chloro-diethanolamine, N-chloro ethylene diamine tetraacetic acid (in this compound the nitrogen atom apparently functions as a quaternary nitrogen).

The preferred compound to be prepared is N-monochloroglycine since while it is relatively unstable it apparently has the proper stability characteristics to function well for the purposes outlined above.

The N-bromo and N-iodo compounds used have shorter half lifes than the corresponding N-chloro compounds.

The N-halo nitrogen compounds used as starting materials are conveniently prepared by reacting a hypohalite with the amino compound in the manner set forth in my copending application entitled "Dental Treatment" filed on even date.

The half life times of aqueous compositions containing N-halo compounds formed in situ and useful in the present invention as either starting materials or final products are those set forth in example 1 below. The half life times are for the N-halo compound and are in minutes except when $h$ indicates hours and $d$ indicates days.

EXAMPLE 1

| Exp. | Nitrogen Compound | Amt. | NaOH Amt. | NaCl Amt. | NaOCl Amt. | 50% Decomposed |
|---|---|---|---|---|---|---|
| 1 | Glycine | 0.05 | 0.05 | 0.05 | 0.0078 | 53.8 |
| 2 | Glycine | 0.0444 | 0.0444 | 0.0615 | 0.0069 | 52.3 |
| 3 | Glycine | 0.1 | 0.1 | 0.115 | 0.156 | 20.0 |
| 4 | Glycine | 0.05 | 0.05 | 0.065 | 0.0078 | 44.2 |
| 5 | Glycine | 0.025 | 0.025 | 0.040 | 0.0039 | 110.2 |
| 6 | Glycine | 0.0125 | 0.0125 | 0.0279 | 0.0020 | 212.0 |
| 7 | Glycine | 0.005 | 0.05 | 0.05 | 0.0078 | 6.3 |
| 8 | Ethanolamine | 0.05 | 0.05 | 0.05 | 0.0078 | 472.0 |
| 9 | Taurine | 0.05 | 0.05 | 0.05 | 0.0078 | 128.4 h |
| 10 | N-acetyl glycine | 0.05 | 0.05 | 0.05 | 0.0078 | 885.0 |
| 11 | Sarcosine | 0.05 | 0.05 | 0.05 | 0.0078 | 108.0 |
| 12 | Sulfamic acid | 0.05 | 0.05 | 0.05 | 0.0078 | 21 d (for 25% decomposition) |
| 13 | L(+)Glutamic acid | 0.05 | 0.05 | 0.05 | 0.0081 | 25.3 |
| 14 | L(+)Glutamic acid | 0.05 | 0.10 | 0.05 | 0.0081 | 42.8 |
| 15 | DL - Aspartic acid | 0.05 | 0.10 | 0.05 | 0.0081 | 32.8 |
| 16 | L+ Lysine | 0.05 | 0.05 | 0.05 | 0.0081 | 107.0 |

| Exp. | Nitrogen Compound | Amt. | NaOH Amt. | NaCl Amt. | NaOCl Amt. | 50% Decomposed |
|------|---|---|---|---|---|---|
| 17 | L– Leucine | 0.05 | 0.05 | 0.05 | 0.0081 | 58.9 |
| 18 | EDTA | 0.05 | 0.10 | 0.05 | 0.0080 | 13.0 |
| 19 | DL Threonine | 0.05 | 0.05 | 0.05 | 0.0080 | 34.9 |
| 20 | L (−) Cystine | 0.05 | 0.1 | 0.05 | 0.0080 | 2.4 |
| 21 | DL-Serine | 0.05 | 0.05 | 0.05 | 0.0080 | 51.9 |
| 22 | L.(+) Cystine | 0.05 | 0.05 | 0.05 | 0.008 | completely decomposed in less than 1 min. |
| 23 | L-Valine | 0.05 | 0.05 | 0.05 | 0.008 | 75.2 |
| 24 | 4-hydroxyproline | 0.05 | 0.05 | 0.05 | 0.008 | 3.0 |
| 25 | DL-Methionine | 0.05 | 0.0501 | 0.05 | 0.008 | 1.3 |
| 26 | L (−) Proline | 0.05 | 0.05 | 0.05 | 0.008 | 1.8 |
| 27 | DL - Alanine | 0.05 | 0.05 | 0.05 | 0.008 | 54.2 |
| 28 | L (+) Arginine | 0.05 | 0.0657 | 0.05 | 0.008 | 48.0 |
| 29 | L - Histidine | 0.05 | 0.0528 | 0.05 | 0.008 | 39.8 |
| 30 | L - Isoleucine | 0.05 | 0.0590 | 0.05 | 0.008 | 76.5 |
| 31 | DL - Phenylalanine | 0.05 | 0.054 | 0.05 | 0.008 | 37.9 |
| 32 | L - Asparagine | 0.05 | 0.0535 | 0.05 | 0.008 | 13.8 |
| 33 | L (+) Glutamine | 0.05 | 0.0537 | 0.05 | 0.008 | 28.0 |
| 34 | DL Ornithine hydrochloride | 0.05 | 0.089 | 0.011 | 0.008 | 38.9 |
| 35 | Aniline - 2 - sulfonic acid | 0.05 | 0.05 | 0.05 | 0.008 | 5.0 |
| 36 | Sulfanilic acid | 0.05 | 0.05 | 0.05 | 0.008 | 1.1 |
| 37 | Metanilic acid | 0.05 | none | 0.05 | 0.008 | 1.25 |
| 38* | Glycine | 0.05 | 0.05 | 0.05 | 0.0079 | 91.4 |
| 39* | Glycine | 0.05 | 0.025 | 0.025 | 0.0038 | 36.2 |
| 40 | N-octadecanylglycine | 0.05 | 0.05 | 0.05 | 0.008 | ** |
| 41 | Aminomethanesulfonic acid | 0.05 | 0.05 | 0.05 | 0.008 | |
| 42 | N-glyclcine | 0.05 | 0.05 | 0.05 | 0.008 | *** |
| 43 | N,N¹-glycylglycylglycine | 0.05 | 0.05 | 0.05 | 0.008 | less than 3 min. |

*In Experiment 38 in place of the sodium compounds there were used the corresponding lithium compounds LiOH, LiOH, and LiOCl) and in Experiment 39 in place of the sodium compounds there were used the corresponding calcium compounds (Ca (OH)$_2$, Ca Cl$_2$ and Ca (OCl)$_2$ ).
**Titration impossible - emulsion developed
***Titration impossible - color developed

EXAMPLE 2

N-monochloroglycine was prepared by making an aqueous mixture from 1 liter of a 0.01 molar N-chlorotaurine solution and 1 liter of a solution which was 0.1 molar in glycine and 0.1 molar in NaCl. The mixed solution had an initial pH of 11.3. The N-chloroglycine was formed very rapidly. The solution formed had 0.01 mole of N-chloroglycine, 0.01 mole of taurine, 0.09 mole of glycine and 0.1 mole of NaCl.

In place of N-chlorotaurine in this example there could be used N-bromo taurine (to form N-bromoglycine for example) or N-acetyl-N-chloro glycine, N-chloro sulfamic acid, N-chloro lysine for example to form N-chloroglycine.

If N-chloroglutamic acid is used in the example the product contains both N-chloroglycine and unchanged N-chloroglutamic acid.

If N-chloroglycine is used with cystine for example there is formed N-chlorocystine.

What is claimed is:

1. A method of forming a first N-monohaloamine comprising reacting in aqueous solution a second N-monohaloamine with a N-halo free amine corresponding to said first N-haloamine, said second N-haloamine having a stability in aqueous solution substantially equal to or greater than the stability of the first N-monohaloamine and being selected from the group consisting of N-halosulfamic acids and N-halo organic nitrogen compounds having 2–11 carbon atoms and selected from the group consisting of N-haloamines containing a hydroxy group, a sulfonic acid group, a carboxylic acid group and an N-acetyl group, said N-halo-free amine having 2–11 carbon atoms and containing a carboxylic acid group, and said halogen having an atomic weight of 35 to 127.

2. A method according to claim 1 wherein the halogen on the first N-monohaloamine is chlorine.

3. A method according to claim 1 wherein the second N-monohaloamine is of greater stability than said first N-monohaloamine in aqueous solution.

4. A method according to claim 3 wherein said second N-haloamine is N-chloroethanolamine, N-chlorotaurine, N-chloro, N-acetyl glycine or N-chlorosulfamic acid and said first N-haloamine is N-chloroglycine, N-chlorosarcosine, N-chloroglutamic acid, N-chloroaspartic acid, N-chlorolysine, N-chloroleucine, N-chlorothreonine, N-chloroserine, N-chlorovaline, N-chloroalanine, N-chloroarginine, N-chlorohistidine, N-chloroisoleucine, N-chlorophenylalanine, N-chloroglutamine, N-chloroasparagine or N-chloroornithine.

5. A method according to claim 3 carried out at a pH of 8 to 12.

6. A method according to claim 5 wherein the pH is 10.5 to 11.5.

7. A method of forming a first N-monochloroamine which is N-chloroglycine, N-chlorosarcosine, N-chloroalpha-aminobutyric acid N-chloralanine, N-chlorobeta-alanine, N-chloroserine, N-chlorophenyl alanine, N-chloronorvaline, N-chloroleucine, N-chloroisoleucine, N-chloroproline, N-chlorohydroxyproline, N-chloroomega-aminoundecanoic acid, N-chloroaspartic acid, N-chloroglutamic acid, N-chloroglutamine, N-chloroasparagine, N-chlorovaline, N-chlorotyrosine, N-chlorothreonine, N-chlorocysteine, N-chlorocystine, N-chloromethionine, N-chlorotryptophane, N-chlorohistidine, N-chloroarginine, N-chlorolysine, N-chlorogamma-aminobutyric acid, N-chloroalpha, epsilon-diaminopimelic acid, N-chloroornithine, N-halo hydroxylysine, N-chloro-anthranilic acid, N-chloro p-aminobenzoic acid, N-chloro ethylenediamine tetraacetic acid or N-chloronitrilotriacetic acid comprising reacting in aqueous solution (1) a second N-monochloroamine having a stability in aqueous solution of substantially equal to or greater than the stability of the first N-monochloroamine and which is N-chlorosulfamic acid or an N-chloro-organic nitrogen compound having 2 to 11 carbon atoms which contains a sulfonic acid group, a hydroxy group, a carboxylic acid group or an N-acetyl group with (2) an N-chloro-free amine corresponding to said first N-chloroamine and which free amine is glycine, sarcosine, alanine, norvaline, leucine, isoleucine, phenyl alanine, alpha-aminobutyric acid, beta-alanine, serine, proline, hydroxyproline, omega-amino-undecanoic acid, aspartic acid, glutamic acid, glutamine, asparagine, valine, tyrosine, threonine, cysteine, cystine, methionine, tryptophane, histidine, arginine, lysine, gamma-aminobutyric acid, alpha, epsilon-diaminopimelic acid, ornithine, hydroxylysine, anthranilic acid, p-aminobenzoic acid, ethylene diamine tetraacetic acid or nitrilotriacetic acid.

8. A method according to claim 7 wherein the free amine is glycine, sarcosine, alpha-aminoisobutyric acid, alanine, beta-alanine, serine, norvaline, leucine, isoleucine, omega-aminoundecanoic acid, aspartic acid, glutamic acid, glutamine, as paragine, valine, threonine, cysteine, cystine, methionine, arginine, lysine, alpha-aminobutyric acid, gamma-aminobutyric acid, alpha-, epsilon diaminopimelic acid, ornithine, hydroxylysine, ethylene diamine tetraacetic acid or nitrilotriacetic acid.

9. A method of forming a first N-monochloroamine which is an unsubstituted N-chloro monoaminoalkanoic acid containing 2 to 11 carbon atoms comprising reacting in aqueous solution a second N-monochloroamine with an N-halo free amine corresponding to said first N-monohaloamine, said second N-monochloroamine having a stability in aqueous solution substantially equal to or greater than the stability of the first N-monochloroamine and being selected from the group consisting of N-chlorosulfamic acid and N-chloro organic nitrogen compounds having 2 to 11 carbon atoms and selected from the group consisting of N-chloroamines containing a hydroxy group, a sulfonic acid group, a carboxylic acid group and an N-acetyl group, said N-chloro free amine being an unsubstituted monoamino alkanoic acid containing 2 to 11 carbon atoms.

10. A method of forming N-monohaloglycine comprising reacting in aqueous solution (1) a N-monohaloamine of greater stability than N-haloglycine in aqueous solution, which N-monohaloamine is an N-halosulfamic acid or N-haloorganic nitrogen compound having 2 to 11 carbon atoms which contains a sulfonic acid group, a hydroxyl group, a carboxylic acid group or an N-acetyl group with (2) glycine, said halogen having an atomic weight of 35 to 127.

11. A method according to claim 10 wherein said first N-monohaloamine is N-chloroglycine.

12. A method according to claim 11 wherein said second N-haloamine is N-chlorotaurine.

* * * * *